US010063369B1

(12) United States Patent
Murphy et al.

(10) Patent No.: US 10,063,369 B1
(45) Date of Patent: Aug. 28, 2018

(54) TIME SYNCHRONIZATION OF MULTI-MODALITY MEASUREMENTS

(71) Applicant: Verily Life Sciences LLC, Mountain View, CA (US)

(72) Inventors: Mark Murphy, Palo Alto, CA (US); Russell Norman Mirov, Thousand Oaks, CA (US); Michael Jastrzebski, Fremont, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

(21) Appl. No.: 15/381,646

(22) Filed: Dec. 16, 2016

Related U.S. Application Data

(60) Provisional application No. 62/268,061, filed on Dec. 16, 2015.

(51) Int. Cl.
*H04L 7/00* (2006.01)
*H04L 7/04* (2006.01)

(52) U.S. Cl.
CPC ..................... *H04L 7/04* (2013.01)

(58) Field of Classification Search
CPC .......... H04B 2001/6908; H04B 1/7176; H04B 1/69; H04B 1/719; H04B 14/026; H04B 14/02; H04L 25/4902; H04L 7/0008; H03K 7/04; H03K 9/04; G06F 1/10; H04J 3/0685; H04J 3/0688; H04J 3/0638
USPC .......................... 375/130, 138, 239, 354–376
See application file for complete search history.

(56) References Cited

U.S. PATENT DOCUMENTS

| | | | | |
|---|---|---|---|---|
| 5,914,991 A | * | 6/1999 | Gigandet | H03L 7/0993 375/355 |
| 6,169,761 B1 | * | 1/2001 | Marcoccia | H04B 1/7156 375/132 |
| 6,204,813 B1 | * | 3/2001 | Wadell | A63B 24/0021 342/463 |
| 6,677,858 B1 | * | 1/2004 | Faris | G06Q 30/06 340/573.1 |
| 6,963,306 B2 | * | 11/2005 | Spilker, Jr. | G01S 5/0036 342/357.29 |
| 6,970,916 B1 | * | 11/2005 | Philyaw | G06Q 30/02 709/217 |
| 7,342,538 B2 | * | 3/2008 | Zimmerman | G01S 5/009 342/357.27 |

(Continued)

*Primary Examiner* — James M Perez
(74) *Attorney, Agent, or Firm* — Kilpatrick Townsend & Stockton LLP

(57) ABSTRACT

The present disclosure is directed to waveform synchronization in multi-modal sensor networks. An example method includes providing a reference signal to a translation circuit. The method also includes generating, by the translation circuit, (i) a first synchronization signal capable of exciting a first emitter to produce a first wave in a first modality and (ii) a second synchronization signal capable of exciting a second emitter to produce a second wave in a second modality, wherein a modality is a domain within a form of energy. The method further includes producing, by the first emitter, first wave in the first modality and, by the second emitter, the second wave in the second modality, wherein the first wave is substantially directed toward a first sensor capable of interacting with the first wave, and wherein the second wave substantially directed toward a second sensor capable of interacting with the second wave.

28 Claims, 8 Drawing Sheets

(56) References Cited

U.S. PATENT DOCUMENTS

| | | | | |
|---|---|---|---|---|
| 7,519,811 B1* | 4/2009 | Hara | ............... | H04H 20/74<br>380/200 |
| 8,114,021 B2* | 2/2012 | Robertson | ............ | A61B 5/0006<br>600/300 |
| 8,565,359 B2* | 10/2013 | Valadon | ............. | H04L 25/0228<br>375/147 |
| 8,812,063 B2* | 8/2014 | Budianu | ............... | H03K 5/082<br>375/342 |
| 9,385,752 B2* | 7/2016 | Loghin | ............... | H03M 13/036 |
| 9,504,425 B2* | 11/2016 | Jooste | ................ | A61B 5/6898 |
| 9,641,469 B2* | 5/2017 | Choudhary | .......... | H04L 51/046 |
| 9,692,630 B2* | 6/2017 | Qi | ..................... | H04L 27/2649 |
| 9,699,607 B2* | 7/2017 | Markhovsky | ........ | H04W 4/023 |
| 9,936,908 B1* | 4/2018 | Acosta | ............... | A61B 5/14556 |
| 2002/0165733 A1* | 11/2002 | Pulkkinen | ........... | G06F 19/321<br>705/2 |
| 2003/0156624 A1* | 8/2003 | Koslar | .................... | H04B 1/69<br>375/131 |
| 2003/0227386 A1* | 12/2003 | Pulkkinen | ............. | A61B 5/1113<br>340/573.1 |
| 2004/0179510 A1* | 9/2004 | Kuffner | ................ | G06K 7/0008<br>370/350 |
| 2004/0203697 A1* | 10/2004 | Finn | ...................... | G08C 17/02<br>455/420 |
| 2006/0088081 A1* | 4/2006 | Withington | ........ | H04B 1/71635<br>375/130 |
| 2006/0200743 A1* | 9/2006 | Thong | ................... | G11B 27/10<br>715/203 |
| 2007/0260286 A1* | 11/2007 | Giftakis | .............. | A61B 5/0402<br>607/9 |
| 2007/0265677 A1* | 11/2007 | Giftakis | .............. | A61B 5/0402<br>607/45 |
| 2008/0064968 A1* | 3/2008 | Martin | ................. | A61B 5/0048<br>600/493 |
| 2008/0244676 A1* | 10/2008 | DaCosta | ............ | H04N 7/17318<br>725/116 |
| 2010/0158076 A1* | 6/2010 | Snlyely | ................ | H04B 1/7075<br>375/130 |
| 2011/0043614 A1* | 2/2011 | Kitazato | ............ | H04N 13/0059<br>348/51 |
| 2012/0016179 A1* | 1/2012 | Paradis | ................ | A61H 9/0078<br>600/17 |
| 2012/0075439 A1* | 3/2012 | Gong | .................... | H04N 5/247<br>348/61 |
| 2012/0254684 A1* | 10/2012 | Loghin | ............... | H03M 13/253<br>714/752 |
| 2012/0320994 A1* | 12/2012 | Loghin | .................. | H03M 13/11<br>375/240.27 |
| 2013/0184538 A1* | 7/2013 | Lee | ...................... | A61B 5/1123<br>600/301 |
| 2013/0230112 A1* | 9/2013 | Schwager | ............. | H04B 3/542<br>375/257 |
| 2013/0254828 A1* | 9/2013 | Reimers | ............ | H04N 21/2385<br>725/134 |
| 2014/0159922 A1* | 6/2014 | Maliszewski | ........... | H04Q 9/00<br>340/870.16 |
| 2015/0173666 A1* | 6/2015 | Smith | ..................... | A61B 5/11<br>600/301 |
| 2015/0280861 A1* | 10/2015 | Qi | .................... | H03M 13/6306<br>714/776 |
| 2016/0307335 A1* | 10/2016 | Perry | ................... | G06T 7/2093 |
| 2017/0086778 A1* | 3/2017 | Cahan | ..................... | A61B 7/02 |
| 2017/0188869 A1* | 7/2017 | Kale | ..................... | A61B 5/0468 |

* cited by examiner

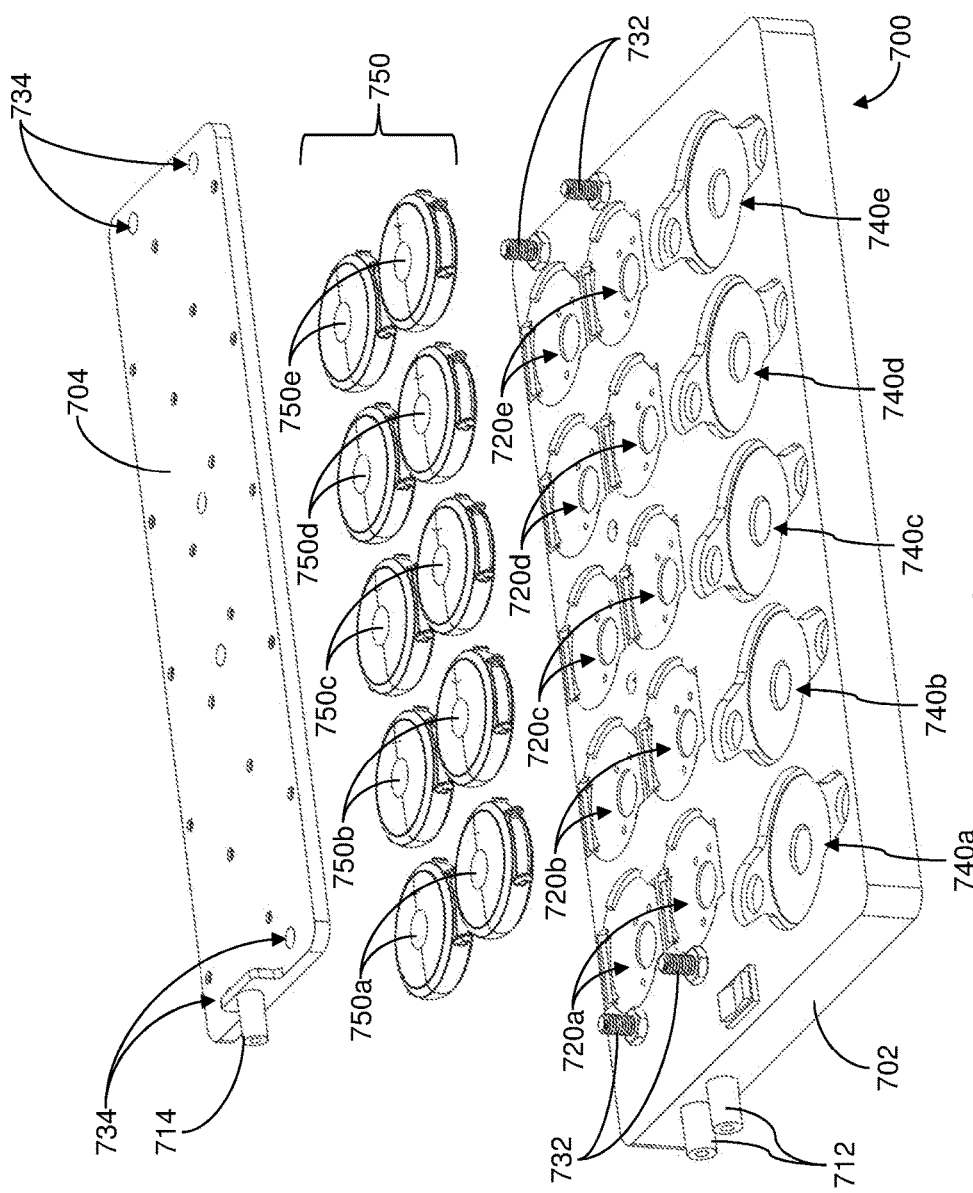

TIME SYNCHRONIZATION OF MULTI-MODALITY MEASUREMENTS

CROSS-REFERENCE TO RELATED APPLICATIONS

This application claims the benefit of U.S. Provisional Patent Application Ser. No. 62/268,061, filed Dec. 16, 2015, which is hereby incorporated by reference in its entirety.

BACKGROUND

Unless otherwise indicated herein, the materials described in this section are not prior art to the claims in this application and are not admitted to be prior art by inclusion in this section.

Sensors are often used to detect and measure waves and disturbances manifest in a particular form of energy. Some sensing devices include electronic components for facilitating the recording of information representative of measurements captured by the sensing device. For example, a sensing device might include an analog-to-digital converter (ADC) for converting analog measurements to digital data. Operation of a ADC typically involves sampling analog measurements against a clock in order to quantize analog measurements to form discrete-time signal data. The clock may server as a reference to which data recorded by one sensor may be synchronized against another reference.

In practice, clock devices are susceptible to clock drift—instabilities in the clock's frequency that causes it to deviate from an intended frequency—resulting from differences in design, manufacturing imperfections, and environmental conditions. In some sensor networks, each sensing device might include its own separate clock, each of which can drift with respect to the other clocks in the network. As the clocks in such a network drift, the time values assigned to data recorded by the sensors becomes increasingly out of phase. Therefore, the integrity of timing-sensitive data may be adversely affected in sensor networks with out-of-sync clocks. Such imprecision may be undesirable in circumstances where the relative timing of events measured across multiple sensors is of interest.

SUMMARY

The present application discloses embodiments that relate to synchronization of measurements in multi-modality sensor networks. In one aspect, the present application describes a method. The method involves providing a reference signal to a translation circuit. The method also involves generating, by the translation circuit based on the reference signal, (i) a first synchronization signal capable of exciting a first emitter to produce a first wave in a first modality and (ii) a second synchronization signal capable of exciting a second emitter to produce a second wave in a second modality. A modality may be a domain within a form of energy. The first modality is different from the second modality. The method further involves producing, by the first emitter, first wave in the first modality and, by the second emitter, the second wave in the second modality. The first wave is substantially directed toward a first sensor capable of interacting with the first wave. The second wave is substantially directed toward a second sensor capable of interacting with the second wave.

In another aspect, the present application describes a system. The system includes a signal generator, a translation circuit, a first emitter, a second emitter, a first sensor, and a second sensor. The signal generator is operable to generate a reference signal. The translation circuit is operable to convert the reference signal into a first synchronization signal and a second synchronization signal. The first synchronization signal includes characteristics that excite emitters in a first modality. The second synchronization signal includes characteristics that excite emitters in a second modality. A modality is a domain within a form of energy. The first modality is different from the second modality. The first emitter is operable to receive the first synchronization signal and responsively produce a first synchronization wave in a first modality. The second emitter is operable to receive the second synchronization signal and responsively produce a second synchronization wave in a second modality. The first sensor is operable to capture at least a portion of the first synchronization wave. The second sensor is operable to capture at least a portion of the second synchronization wave.

In a further aspect, the present application describes a method. The method involves producing, by a first emitter, a first wave in a first modality. The method also involves producing, by a second emitter, a second wave in a second modality. A modality is a domain within a form of energy. The first modality is different from the second modality. The method further involves capturing, by a first sensor, a first waveform including at least a portion of the first wave, wherein the first segment begins at a first time offset relative to the start of the first waveform. Additionally, the method involves capturing, by a second sensor, a second waveform including at least a portion of the second wave. The second segment begins at a second time offset relative to the start of the second waveform. Further, the method involves providing a time-synchronized output indicative of at least one of (i) a portion of the first waveform and (ii) a portion of the second waveform based on at least the first time offset and the second time offset.

In yet a further aspect, the present application describes a system for synchronizing a plurality of sensing devices, e.g., electrocardiogram (ECG) electrodes. The system includes a signal generator operable to generate a reference signal. The system also includes a synchronization device coupled to the signal generator and configured to receive the reference signal from the signal generator. The synchronization device includes a plurality of receptacles configured to engage a plurality of sensing devices and simultaneously transmit the same reference signal to the plurality of sensing devices. The sensing devices are configured to detect and store the same reference signal with a respective timestamp, wherein the respective timestamps indicate time offsets between data collected by the sensing devices.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE FIGURES

FIG. 7A illustrates a view of an example synchronization device for synchronizing a plurality of sensing devices, according to an example embodiment.

DETAILED DESCRIPTION

Figure 1:
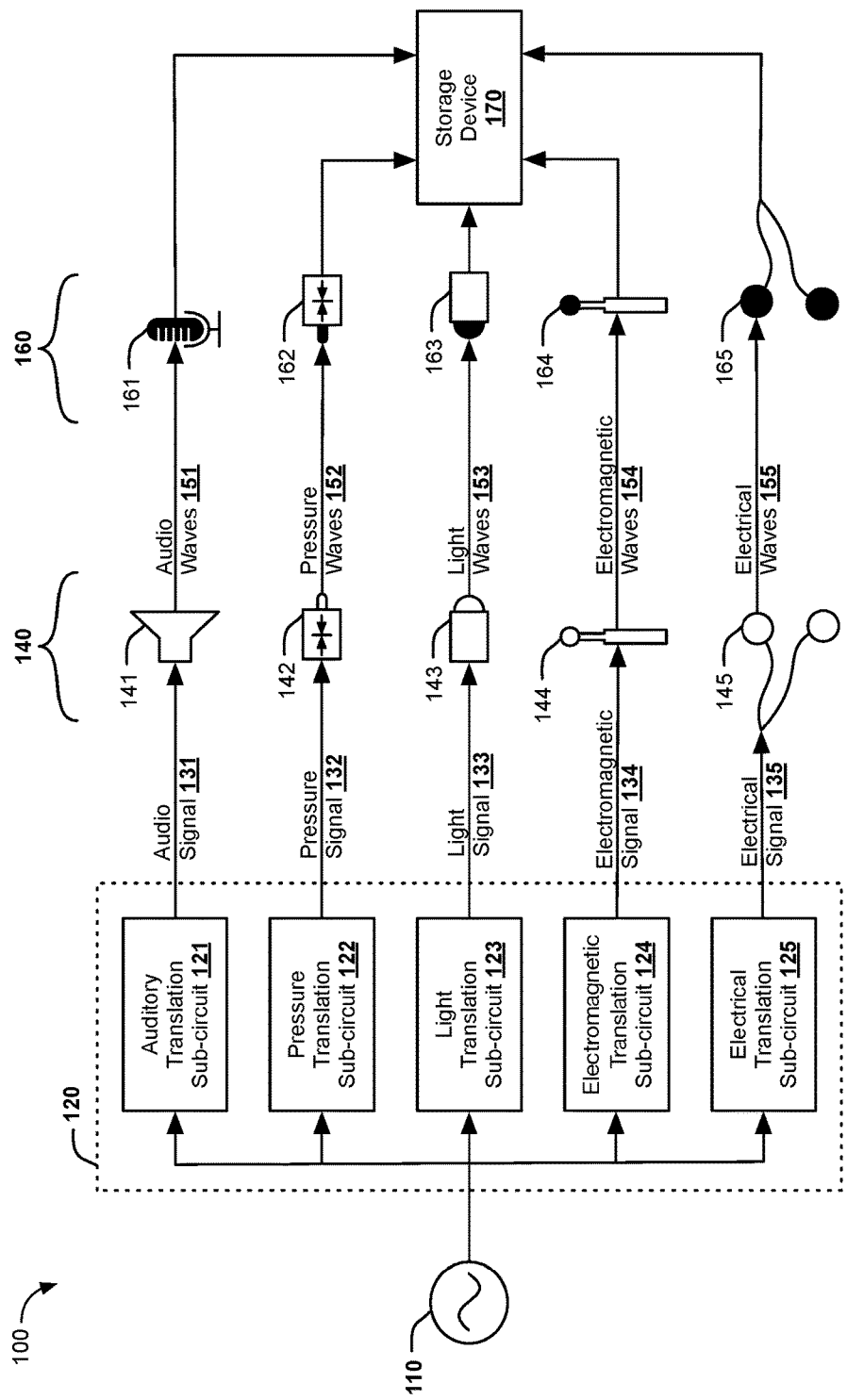
FIG. 1 is a functional block diagram illustrating an example system, according to an example embodiment.

Example methods and systems are described herein. Any example embodiment or feature described herein is not necessarily to be construed as preferred or advantageous over other embodiments or features. The example embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments might include more or less of each element shown in a given Figure. Further, some of the illustrated elements may be combined or omitted. Yet further, an example embodiment may include elements that are not illustrated in the Figures.

I. Overview

Sensors may operate by detecting disturbances within a modality, in which the disturbances excite the sensor, causing fluctuations in the sensor's output current, voltage, or capacitance. Such sensors are often coupled to a separate device for interpreting the output. To collect and store digital sensor information, such devices (sometimes referred to as "data acquisition systems") typically employ electronic components for digitizing the sensor's analog output and storing the resulting data. In these configurations, a data acquisition system or the like may operate based off a master clock, allowing the data captured from different sensors to be synchronized in time.

However, as sensing devices have become increasingly sophisticated, electronic components typically found in data acquisition systems may now be embedded within the sensing device. These advancements in sensor technology have enabled sensor networks to be more ad-hoc than before. Instead of being tethered to a data acquisition system, the sensors in an ad-hoc network may collect sensor data, store that data, and even wirelessly transmit the data to separate systems. Such sensing devices may be added and/or removed from a sensor network as needed without significant reconfiguration.

Each sensing device in an ad-hoc sensor network may be driven by its own independent clock. The operational frequency of each of these clocks may differ from each other. Additionally, such sensing devices may be activated at different times, such that one sensing device may begin recording data while another sensing device has already been recording data for some time. Due to the differences in clock frequency, clock phase, and recording start and stop times, it may be difficult to determine a synchronized time alignment across data recorded by separate sensing devices.

An example synchronization technique involves generating and emitting synchronization pulses or waves in two or more modalities, directed toward sensors that measure disturbances in those two or more modalities. The synchronization pulses or waves may have known or predetermined characteristics—such as a known duration, known frequencies and/or amplitudes—which enable them to be filtered or otherwise identified from measurements captured by the sensors. The sensors may capture and record waveforms, where at least a portion of the recorded waveforms include the synchronization pulses or waves. The recorded waveforms can then be analyzed to detect the time location of the synchronization pulses or waves, which may serve as a basis for aligning two or more sensor waveforms, modifying the time data of one or more sensor waveforms, and/or for further secondary analyses such as characterizing a causal chain of events in multiple modalities.

An example system for producing synchronization pulses or waves in multiple modalities includes a signal generator, a translation circuit, and emitters capable of producing the synchronization pulses or waves in the multiple modalities. A signal generator may initially generate a reference signal, which is provided as an input to a translation circuit. The translation circuit may include electronic components for converting the reference signal into two or more synchronization signals—each of which having characteristics suitable for exciting a respective transducer to produce a waveform in a respective modality—and provide the two or more synchronization signals to corresponding emitters. The emitters may then, upon being excited by the synchronization signals, emit the synchronization pulses or waves.

More specifically, the translation circuit may convert the reference signal by modifying its frequency and/or amplitude to comply with a particular modality. The reference signal may be an analog or digital signal, and the translation circuit may, in some instances, include analog-to-digital converters (ADCs) and/or digital-to-analog converters (DACs). As one example, the translation circuit may convert a 1 kHz reference signal to a 30 kHz audio synchronization signal, which may then be provided to a high frequency speaker to be emitted as an ultrasonic synchronization wave. As another example, the translation circuit may convert an analog 1 kHz reference signal to a digital 1 kHz reference signal that switches between a low and high voltage for activating and deactivating a light emitting diode (LED).

In some implementations, the signal generator may generate a reference signal that changes over time. In one example, the signal generator may generate a pseudorandom waveform, which may be stored and used as a basis for later synchronization. In another example, the signal generator may produce a known or predetermined time-varying waveform pattern or pulse train. The translation circuit may include electrical components, integrated circuits, and/or processors for converting a time-varying reference signal to a time-varying synchronization signal in a particular domain. For example, varying amplitudes in an analog reference signal may be conveyed as digital information in a synchronization wave. The specific manner in which analog-to-digital and digital-to-analog conversions are carried out may vary among implementations; it should be understood that the manner of conversion in a particular implementation may be known by computing devices that process and synchronize data captured by sensors.

Waves in certain modalities may travel faster than waves in other modalities. For instance, electromagnetic waves may travel at or near the speed of light, whereas pressure waves may travel many orders of magnitude slower. Thus, in some implementations, the translation circuit (or another separate component operationally coupled to the translation circuit) may delay the emission of a synchronization pulse or wave. In scenarios where the sensor arrangement is known or predetermined, the translation circuit may vary the timing of synchronization pulse or wave emissions so that the waves or pulses arrive at their respective sensors simultaneously (or approximately simultaneously).

During operation, sensors within a sensor network may capture disturbances over a period of time. While the sensors are recording, the above-described system may produce synchronization pulses or waves, which may be recorded by the sensors along with other disturbances or measurements. The data generated by these sensors may then be processed to detect the locations of synchronization pulses or waves relative to the recorded waveforms. Based on known aspects of the synchronization scheme, the location of the synchronization pulses or waves in the waveform data may then be associated with an absolute time value. Such absolute time value assignments may serve as a basis for aligning the waveforms.

Waveform alignment may include modifying time information within the data to reflect an absolute time axis, thereby enabling a direct data comparison (e.g., computationally) among two or more separate waveforms. Waveform alignment may also include generating a human-readable graphical output, either on a physical medium or via a graphical user interface portrayed on a display device. In some instances, other computational processes may be performed. For example, the alignment of waveforms may be used to determine a particular metric or measurement, and the waveform alignment may be an intermediate step in process for determining a causal link between events in two or more waveforms. It should be understood that waveform alignment may refer to any process that synchronizes the data for human and/or computational analysis of the waveforms.

As one specific example, a sensor network may be present within a human body and measure various biometrics. For instance, a patient may be monitored using a blood pressure sensor, an electrocardiogram (ECG) sensor, and a fingertip oximeter. If the patient has a certain condition or ailment, such as heart palpitations, such a condition may be better characterized if the sensor data is time aligned. More sensors may be added to the system, such as stethoscopes or additional blood pressure sensors, ECG sensors, or fingertip oximeters. In this example, the above-described synchronization wave technique may be employed to create a common, simultaneous (or near-simultaneous) event in the different modalities (e.g., a pressure wave for the blood pressure sensors, an electrical pulse for the ECG sensors, a light pulse for the fingertip oximeters, and/or an auditory wave for the stethoscopes).

As another specific example, sensing devices within a sensor network may all be capable of measuring disturbances in a common modality, in addition to measuring disturbances in a different modality. For instance, a blood pressure sensor, an ECG sensor, and a fingertip oximeter may all include therein accelerometers. An injected synchronization pulse or wave may be an induced acceleration on the sensors—either from human activity or environmental changes—to generate a common event across multiple sensors. If the accelerometer data is aligned with the other sensory data in a particular sensor (e.g., because both the accelerometer and other transducer in the sensing device are driven by a common clock), then events detected in the accelerometer data may serve as a basis for aligning multi-modality sensor data.

As described herein, "producing" a synchronization pulse or wave may refer to generating the electrical signals for exciting or instructing a transducer to emit the pulse or wave, amplifying such electric signals, transmitting those electrical signals to the transducer, the actual emitting of the pulse or wave, and/or any other step for causing the transducer to emit the pulse or wave.

As described herein, a "modality" may generally refer to a form of energy (or a particular subset that form of energy) within which a synchronization waveform can be emitted and/or detected. Some example forms of energy include kinetic energy, elastic energy, thermal energy, electric energy, magnetic energy, light energy, and a variety of mechanical energies (e.g., pressure waves in various media), among other possible forms of energy.

In some instances, a "modality" may describe a subset of a particular form of energy. For example, one modality may be electromagnetic energy—which can take the form of radio waves, microwaves, infrared light, visible light, ultraviolet light, and/or X-rays, among other forms—which can be detected using a variety of means, such as antennas or photodiodes. More specifically a "modality" may refer to a subset of a particular form of energy, such as visible light (e.g., a range of wavelengths) detected using photodiodes. Some modalities may be defined even more narrowly, such as a laser (e.g., a very narrow wavelength band) detected using a corresponding diode that senses the particular light wavelength emitted by the laser. Thus, two or more modalities may, in some instances, have a common form of energy but represent different ranges within that form of energy.

A modality as described herein may therefore be confined to a particular portion of a form of energy. Some sensors and/or transducers may be designed to operate within a certain range of amplitudes, frequencies, or wavelengths. Thus, a "modality" may refer to a specific operational range through which energy of a particular form may be transmitted and/or sensed.

II. Example Systems

Example systems within the scope of the present disclosure will now be described in greater detail. An example system may include various combinations of sensing devices, emitters, and devices for controlling and driving the emitters. Additionally, an example system may include one or more computing devices for aggregating, storing, and processing data recorded by various sensing devices. Furthermore, an example system may include an output device—such as printers, projectors, digital displays, audio speakers, etc.—for producing text-based and/or graphical representations of time-aligned sensor data.

As described herein, a "sensing device" may be any device capable of measuring disturbances in one or more modalities. Some sensing devices may operate within a single modality, while others include transducers for taking measurements in multiple modalities. Additionally, sensing devices may include electronic components, hardware, and/or software for digitizing analog sensor measurements, storing that data, and/or transmitting that data to a separate device. Transmitting data from a sensing device may be performed via a wired connection, or via a wireless connection if the sensing device includes wireless communication hardware.

FIG. 1 is a block diagram illustrating an example system 100, according to an example embodiment. The system 100 includes a signal generator 110, a multi-modality translation circuit 120, a set of emitters 140, and a corresponding set of sensors 160. During operation, the signal generator 110 generates a reference signal, which is provided as input to the translation circuit 120. The translation circuit 120 may include one or more sub-circuits, each of which converts the reference signal into a signal for exciting an emitter to produce waves in a particular modality. The signals are then provided to respective emitters 140, which may be transducers or other devices that transform received signals (e.g., electronic signals, such as varying voltages and/or currents) into pulses and/or waves of a particular form of energy. The emitted waves may then interact with respective sensors 160, which capture at least part of the emitted waves and records characteristics of those waves to be stored as waveforms (e.g., a time-varying representation of the emitted waves and any other waves incident on the sensors over a period of time). The recorded waveforms may be stored on a storage medium, which may be incorporated within the sensor. In other instances, the recorded waveforms are transmitted—either via a wired or wireless connection—to a separate storage medium, such as storage device 170.

The signal generator 110 may be any combination of hardware and/or software that produces a reference signal. The reference signal may be any signal that may be converted into modality-specific signals. In some embodiments, the reference signal may be a sinusoidal voltage signal having a particular frequency and amplitude (e.g., 44 kHz with 100 mV root mean square (RMS) voltage). In other embodiments, the reference signal's frequency and/or amplitude may vary over a period of time. For example, the reference signal may be a frequency-modulated or amplitude-modulated representation of a sequence of bits, numbers, or other information. The information encoded into the reference signal may, in some cases, be a known sequence, which may also be repeated over a duration of time. In other cases, a random or pseudorandom sequence may be encoded into the reference signal (or a random or pseudorandom analog signal may be generated). In additional implementations, the signal generator 110 may output a digital reference signal (e.g., varying between a high voltage and a low voltage) representing a sequence of bits. In these various implementations, the known sequence or waveform that forms the reference signal may be stored or otherwise replicated at a later time in order to assist in the synchronization of waveforms from multiple modalities. Some synchronization techniques utilizing a known time-varying reference signal are described in greater detail below.

In some embodiments, the signal generator 110 may be implemented as a combination of electrical devices that form a circuit. In other embodiments, the signal generator 110 may include integrated circuits and/or other components that may be programmed to perform certain operations. For instance, the signal generator 110 may include electrical components that permit an input of digital instructions that configure the signal generator 110 to produce a particular reference signal (e.g., a digital signal representing a series of bits, an amplitude-modulated or frequency-modulated analog signal representing encoded information, an analog signal with a constant frequency and amplitude, etc.). In some implementations, the signal generator 110 may include inputs (e.g., terminals or ports) that may receive instructions or signals from other devices—such as computing devices—which cause the signal generator 110 to behave according to one of the above-mentioned behaviors, among other possible behaviors.

In further embodiments, the operations and functionality provided by the signal generator 110 may be substituted with other signal generation means. For example, certain environmental characteristics, events, and/or other signal sources may serve as the reference signal with which the translation circuit 120 generates the various modality-specific signals. Additionally or alternatively, the translation circuit 120 may integrate therein components for either producing the reference signal, or for capturing the reference signal from some other source (e.g., from an environmental source, from one or more events recorded by motion sensors or accelerometers, etc.). It should be understood that the signal generator 110 is one example implementation for producing the reference signal.

The translation circuit 120 may include any combination of hardware and/or software for converting a reference signal into one or more modality-specific signals. In the example system depicted in FIG. 1, the translation circuit includes a set of modality-specific sub-circuits, including auditory translation sub-circuit 121, pressure translation sub-circuit 122, light translation sub-circuit 123, electromagnetic translation sub-circuit 124, and electrical translation sub-circuit 125. Each of these sub-circuits may themselves include a combination of electrical components, integrated circuits, digital components, and/or program instructions that collectively perform the conversion between the reference signal and the modality-specific signal output. Depending upon the particular embodiment and configuration, a sub-circuit may perform analog-to-digital conversion (ADC), digital-to-analog conversion (DAC), amplification or attenuation of the reference signal, frequency conversion (either increasing or decreasing) of the reference signal, and/or any combination thereof.

Regardless of the particular conversion technique, a given sub-circuit may produce a modality-specific signal that is capable of exciting a corresponding emitter. Without conversion, the reference signal may be of insufficient amplitude and/or be of a frequency outside of the operational range of a corresponding emitter, such that attempting to excite the emitter with the reference signal would not produce a wave (or would produce a suboptimal wave output). Conversion of the reference signal may therefore generate an output signal with characteristics specific to a particular modality. Thus, the manner of conversion between reference signals and modality-specific signals may depend upon how a certain modality is defined. A modality may define an operational range of amplitudes and/or frequencies, and the method of conversion may accordingly modify the reference signal such that the output signal's characteristics conform (or at least substantially conform) to that operational range.

The manner of conversion may further be defined by the kinds of measurements recorded by the sensors 160. For example, the microphone 161 may be a stethoscope intended to record acoustic heartbeats in a patient; in such circumstances, the microphone 161 may record auditory waves having frequencies between 20 Hz up to 1 kHz. However, the microphone 161 may be capable of capturing audio signals up to 20 kHz. In this example, the reference signal may be converted such that the resulting audio signal 131 to be emitted by speaker 141 lies outside of the frequency range of heartbeats (e.g., may be converted to signals between 5 kHz and 15 kHz). Thus, in addition to considering the operational range defined by sensors and/or emitters within a modality, the conversion techniques may be application-specific in order to avoid interfering with measurement data. In this manner, synchronization pulses and/or waves may be distinctly filtered from the measurement data.

The auditory translation sub-circuit 121 may convert the reference signal into an audio signal 131. An audio modality may be defined by acoustic waves that may be produced by speakers and/or captured by microphones. As a specific example, an audio modality may be defined from 20 Hz to 20 kHz, among other possible frequency ranges. The audio modality may, in some instances, be defined as detectable pressure waves in a gas medium (e.g., air). Further, the audio modality may include any range of amplitudes that can be produced by speakers and/or captured by microphones. The auditory translation sub-circuit 121 may produce an audio signal 131 that conforms to such an audio modality.

The pressure translation sub-circuit 122 may convert the reference signal into a pressure signal 132. A pressure modality may be defined by pressure waves that may be produced by pressure transducers and/or captured by pressure sensors. As a specific example, a pressure modality may be defined from 1 Hz to 1 kHz, among other possible frequency ranges. The pressure modality may, in some instances, be defined as detectable pressure waves in a liquid (or multi-phase medium). One example implementation might involve capturing blood pressure measurements in a patient, and the pressure modality may be defined at least partially by the operational capabilities of blood pressure sensors. Further, the blood pressure modality may include any range of pressure amplitudes that can be produced by pressure transducers and/or captured by pressure sensors. In some instances, such as those related to medical applications, the range of amplitudes within a pressure modality may be limited so that the pressure levels are safe for patients. The pressure translation sub-circuit 122 may produce the pressure signal 132 that conforms to such a pressure modality.

The light translation sub-circuit 123 may convert the reference signal into a light signal 133. A light modality may be defined by electromagnetic waves having wavelengths that lie at least partially within the visible light spectrum (e.g., 380 nanometers to 750 nanometers, or 400 THz to 789 THz, among other possible ranges). In other implementations, the light modality may also include portions of the infrared and/or ultraviolet light spectrum. The light modality may encompass light intensities that can be produced by light emitters (e.g., light bulbs, lasers, light emitting diodes (LEDs), etc.) and captured by light sensors (e.g., photodiodes, phototransistors, photomultipliers, charge-coupled devices (CCDs), etc.). In some instances, this type of light modality might be referred to as an "optical" modality. The light translation sub-circuit 123 may produce the light signal 133 that conforms to such a light or optical modality.

The light translation sub-circuit 123 may, in some implementations, perform ADC conversion to produce a digital output. For example, the light emitter 141 may be an LED that may be activated when a voltage input meets a threshold voltage and otherwise be off when the voltage input is below that voltage (i.e., the LEDs "turn on" voltage, or band gap). In such implementations, an analog reference signal may produce undesirable results when applied to an LED or other digital light emitting component. The light translation sub-circuit 123 may convert the analog reference signal into a corresponding digital signal, which may either approximately represent the analog reference signal itself, or may be a digital representation of information encoded within the analog reference signal. For instance, the output may be a pulse-width modulated (PWM) signal that approximately represents the analog reference signal itself, such that the PWM light signal 133 effectively produces varying intensities of light (when averaged over time). In other instances, the output may be a digital sequence of bits representative of bits encoded within an analog reference signal (e.g., FM or AM encoding).

The electromagnetic translation sub-circuit 124 may convert the reference signal into an electromagnetic signal 134. The electromagnetic modality may be defined by electromagnetic waves having frequencies within a particular range, such as radio waves or microwaves (e.g., from 3 kHz to 30 GHz). More specifically, a particular electromagnetic modality may be defined by a smaller range of frequencies within a particular band of the electromagnetic spectrum. The electromagnetic modality may encompass wave amplitudes that can emitted and captured by antennas (including omnidirectional and directional antennas). The range of amplitudes within an electromagnetic modality may be limited due to regulatory standards and/or safety considerations. The electromagnetic translation sub-circuit 124 may produce the electromagnetic signal 134 that conforms to such an electromagnetic modality.

Note that, although the electromagnetic modality and the light modality share a common form of energy—electromagnetic waves—frequency ranges are distinct, and the means for producing and measuring waves between the two modalities differs significantly. Additionally, the audio modality and the pressure modality share a common form of energy—mechanical pressures—where the primary difference between the two modalities is the medium in which the pressure waves propagate (liquid or gas). Thus, it should be understood that two modalities may share a common form of energy, yet represent two different domains (e.g., operational ranges, frequencies, amplitudes, analog vs. digital, etc.) within that form of energy. As described herein, the "domain" within a form of energy may be defined as the characteristics that delineate between two modalities having a common form of energy.

The electrical translation sub-circuit 125 may convert the reference signal into an electrical signal 135. The electrical modality may be defined by electrical pulses or waves in a particular medium having detectable voltage and/or current levels. As one specific example, an electrical modality may be defined by the operational range of electrocardiogram (ECG) sensors coupled to a patient. The range of voltage amplitudes, current amplitudes, and/or frequencies may be limited such that the electrical levels are safe for patients. The electrical translation sub-circuit 125 may produce the electrical signal 135 to conform to such an electrical modality.

It should be understood that the various modalities discussed herein are example definitions of modalities, and are provided for explanatory purposes. Other modalities—which may be defined by various domains of various forms of energy not expressly disclosed herein—may also be implemented in a multi-modality sensor synchronization scheme without departing from the scope of this application.

The emitters 140 may each include any combination of hardware and/or software for converting a modality-specific signal into a corresponding modality-specific wave. In some instances, an emitter may be a transducer that is excited by the modality-specific signal, the excitation of which produces the modality-specific wave (e.g., a passive transducer). In other instances, an emitter may be powered and include electronic components for amplifying the modality-specific signal (e.g., an active transducer). Other emitters may be more complex and include electronic components that collectively cause the excitation of an emitter's transducer to produce the wave. For example, an electroacoustic speaker may include a driver, which may include a magnet interfaced with a membrane to produce the acoustic waves. It should be understood that a given emitter may include any combination of components that facilitate the production of waves in a particular modality.

The audio emitter 141 may be any type of electroacoustical transducer that converts the audio signal 131 into the audio wave 151. Some example audio emitters include magnetostatic speakers, piezoelectric speakers, electrostatic speakers, and/or any other device capable to producing audio waves. The resulting audio wave 151 may, in some instances, be at least partially directed toward the microphone 161.

The pressure emitter 142 may be any type of transducer that converts the pressure signal 132 into the pressure wave 152. Some example pressure emitters utilize electric potentials and/or currents from the pressure signal 132 in order to generate mechanical disturbances in a material, which may in turn cause a membrane to oscillate and produce the pressure wave 152. The resulting pressure wave 152 may, in some instances, be at least partially directed toward the pressure sensor 162.

The light emitter 143 may be any type of light source that converts the light signal 133 into the light wave 153. Some example light emitters include filament bulbs, halogen bulbs, fluorescent bulbs, LEDs, and lasers, among other possible light emitters. The resulting light wave 153 may, in some instances, be at least partially directed toward the light sensor 163.

The electromagnetic emitter 144 may be any type of antenna that converts the electromagnetic signal 134 into the electromagnetic wave 154. Some example electromagnetic emitters include omnidirectional antennas (e.g., quarter dipole antennas), directional antennas (e.g., parabolic reflectors), and/or any combination thereof. The resulting electromagnetic wave 154 may, in some instances, be at least partially directed toward the electromagnetic sensor 164 (either due to the omnidirectional nature of the electromagnetic wave 154, or due to directionally "aiming" the electromagnetic wave 154 toward the electromagnetic sensor 164).

The electrical emitter 145 may be any type of conductive device that converts the electrical signal 135 into the electrical wave 155. More specifically, the electrical emitter may be any type of conductive element that can be secured to a medium, such as electric pads and/or electrical connectors. In some applications, such as within the medical field, the electrical emitter 145 may be electrical leads with geometries that are substantially capable of being adhered to portions of a patient's body. The resulting electrical wave 155 may, in some instances, be at least partially directed toward the electrical sensor 165 (via conduction through a medium to which the electrical emitter 145 and the electrical sensor 165 are both coupled).

The sensors 160 may each include any combination of hardware and/or software for converting a modality-specific wave into a corresponding waveform, which may take the form of an analog output or as digital information representative of the waveform. In some implementations, a "sensor" may comprise various electronic components for facilitating ADC conversion of waves into waveform data, storage of that waveform data (either on volatile or non-volatile storage), and/or transmission of the waveform data to a separate storage medium, such as the storage device 170. Although illustrated as transducers, each sensor may include electrical components for recording the captured waveforms.

The microphone 161 may be any electroacoustical transducer that converts the audio waves 151 into audio waveform data. The pressure sensor 162 may be any type of transducer that converts the pressure waves 152 into pressure waveform data. The light sensor 163 may be any type of sensor that converts incident light waves 153 into light waveform data. The electromagnetic sensor 164 may be any type of antenna that converts received electromagnetic waves 154 into electromagnetic waveform data. The electrical sensors 165 may be any type of conductive device that converts the electrical waves 155 into electrical waveform data.

As described herein, a "wave" may include any combination of waves, pulses, or combinations thereof. For instance, a wave may be a sequence of pulses that form a pulse train. In other examples, a wave may be a superposition of multiple waves and/or pulses that interfere with each other to form the resulting wave. It should be understood that "wave" refers to any type of disturbance or fluctuations within a particular form of energy.

A given sensor may include a clock that may drive the ADC conversion and/or may act as a reference to which waveform data may be mapped. As one specific example, a sensor may record samples at a rate of 100 Hz, such that each sample is separated by (approximately) 10 milliseconds (ms). In this example, each sampled data point may be mapped to a time value that is a multiple of the 10 ms period. Such a sensor may include electronic components that output this type of two dimensional data—amplitude data mapped to discrete time values.

However, due to clock drift and other sources of imprecision, the clock may run faster or slower than intended, thereby impacting the sampling rate. Over time, the discrete time values assigned to waveform data points may become offset. However, since sensor networks such as sensor network 100 include independent sensors, each sensor may be driven by its own separate clock. This may be one source of discrete time value inaccuracies in the waveform data produced by the sensors 160.

Sensors described herein may include other electronic components or elements not explicitly depicted in FIG. 1. For example, some sensors may include batteries and/or other energy storage elements for powering the sensors. As another example, some sensors may include components for receiving power wirelessly via conductive coupling. Additionally, sensors may contain electronic components, integrated circuits, and/or antennas to enable communication to a network. Some example wireless communication schemes may include 3G cellular communication, such as CDMA, EVDO, GSM/GPRS, or 4G cellular communication, such as WiMAX or LTE. In some implementations, sensors may communicate over a wireless local area network (WLAN), for example, using WiFi. Additionally, sensors may include buttons, switches, light indicators, display devices, and/or other components to allow the sensor to be activated, deactivated, display status information, and/or otherwise be configured by a user.

The devices illustrated in FIG. 1 may communicate to other devices via wired or wireless connections. In some instances, the signal generator 110 may be directly connected to the translation circuit 120; in other instances, the signal generator 110 may broadcast or be wirelessly coupled to the translation circuit 120, which could wirelessly receive the reference signal. The modality-specific signals may be transmitted over a wired connection to its respective emitter, or be wirelessly transmitted to its emitter. Each of the modality-specific waves may be emitted in all directions, or may be focused in a particular direction (either through beamforming techniques or mechanical focusing elements, such as dishes, waveforms, tubes, etc.). Furthermore, each sensor may include wired and/or wireless interfaces through which waveform data may be transmitted to other computing devices or storage devices.

Although FIG. 1 illustrates various translation sub-circuits, emitters, and sensors, other types of conversion devices, transducers, electronic components, sub-circuits, emitters, and/or sensors may also be included without departing from the scope of the present application.

Figure 7B:
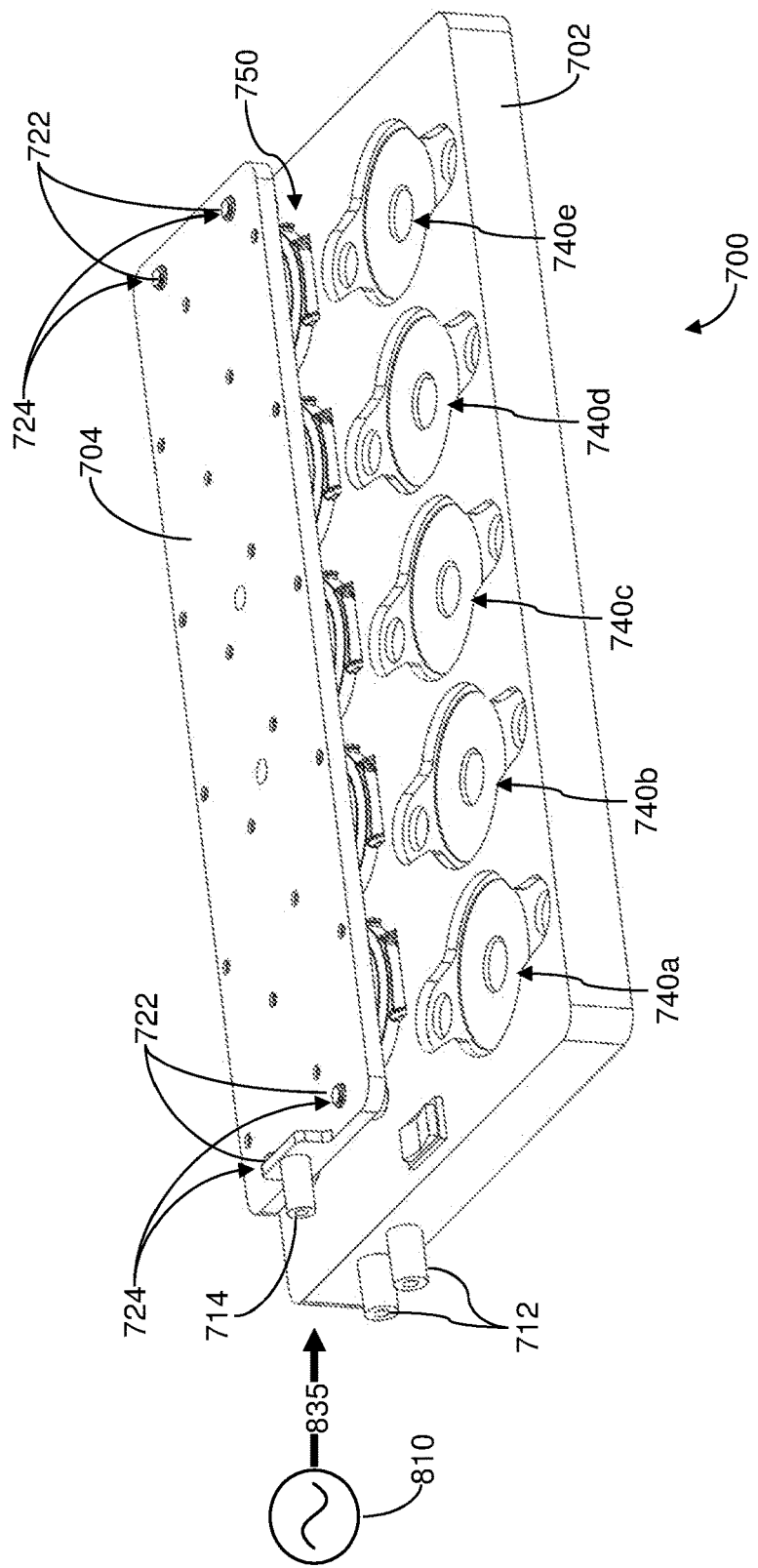
FIG. 7B illustrates another view of the example synchronization device of FIG. 7A.

FIGS. 7A-B illustrate an example synchronization device 700 for synchronizing a plurality of ECG electrodes 750. As FIG. 7A illustrates in particular, the electrodes 750 include five electrode pairs 750a-e. Each of the electrode pairs 750a-e may be employed to monitor a patient's electrocardio activity as a function of time. For instance, one of the electrode pairs 750a-e may be attached to a chest strap. When worn by a patient, the chest strap positions the pair of electrodes 750 against the skin of the patient's chest and establishes electrical conductivity between the electrodes 750 and the skin. The electrodes 750 can detect and record, in time order, data relating to electrocardio activity generated by heart muscle depolarizations, which propagate in pulsating electrical waves towards the skin. The synchronization device 700 provides a reference signal that allows the electrocardio data collected by multiple sensors 750 to be synchronized.

According to some implementations, synchronization by the device 700 allows more precise correlation and comparison of electrocardio data collected from each of a pair of electrodes 750 coupled to a single patient. Such comparison may reveal measurement and other errors in the data and allow the collected data to be adjusted for more accurate indications of electrocardio activity.

In other implementations, the electrode pairs 750a-e may be employed in a study of several patients. In such a study, it may be useful to correlate and analyze the data collected across the several patients. Advantageously, the synchronization device 700 allows all electrode pairs 750a-e to be synchronized with the same reference signal, thereby allowing the data from all electrodes 750 to be more easily correlated and compared.

The synchronization device 700 includes a base 702 and a top plate 704. The base 702 includes receptacles 720 to receive the electrodes 750. In particular, five pairs of receptacles 720a-e are configured to engage the five electrode pairs 750a-e, respectively. When the electrodes 750 are disposed in the receptacles 720, the top plate 704 can be positioned over the base 702 and into contact with the electrodes 750 as shown in FIG. 7B. The base 702 includes pins 732 that extend upwardly, and the top plate 704 includes corresponding apertures 734 that can receive the pins 732. As such, the pins 732 can guide the top plate 704 as the top plate 704 is positioned over the base 702.

The base 702 and the top plate 704 include respective connectors 712, 714 that can be electrically coupled to a signal generator 810. The signal generator 810 may include aspects of the signal generator 110 described above. In particular, the signal generator 810 can generate an electrical signal 835 having an identifiable waveform. The synchronization device 700 can receive the electrical signal 835 via the connectors 712, 714. When assembled as shown in FIG. 7B, the base 702, the top plate 704, and the electrodes 750 form electrically conductive paths that allow each electrode 750 to detect and record the electrical signal 835 from the signal generator 810. Because each electrode 750 records the same identifiable electrical signal 835, the electrical signal 835 can act as a reference signal for correlating data stored across the multiple electrodes 750. Each electrode 750 may also include a clock that can provide a timestamp for the recorded reference signal 835.

After recording the reference signal 835, the electrodes 750 may be employed in pairs to collect electrocardio data from patients. For instance, the five electrode pairs 750a-e may be employed to collect electrocardio data from up to five patients. The data stored by the electrodes 750 includes, in time order, the reference signal 835 from the signal generator 810 as well as the electrocardio data. As described above, the reference signal 835 is a waveform that is distinctly identifiable from the electrocardio activity. When evaluating the data stored on multiple electrodes 750, the streams of data from the multiple electrodes 750 can be aligned according to the reference signals 385 also present in the streams of data. Once the streams of data are thus aligned, time offsets between the multiple electrodes 750 can be determined to allow the streams of data to be accurately correlated and compared.

The synchronization device 700 is not limited to synchronizing the electrodes 750. Indeed, as shown in FIGS. 7A-B, the base 702 includes five additional receptacles 740a-e configured to receive additional sensor devices. The synchronization device 700 can also transmit the reference signal 835 from the signal generator 810 for storage by these additional sensor devices. These additional sensor devices may include a clock that can provide a timestamp for the stored reference signal 835.

According to one implementation, each electrode pair 750a-e is combined with a monitoring device (not shown) that can also be worn by the patient. As such, the five receptacles 740a-e may be configured to engage five monitoring devices where the monitoring devices can receive and record the same reference signal 835 from the signal generator 810.

The monitoring devices may have a form factor that is similar to that of a wristwatch. When worn by the patient, the monitoring device receives and processes data from the corresponding pair of electrodes 750 positioned against the patient's chest. The monitoring device is preferably synchronized with the pair of electrodes 750, so that the data from the monitoring device can be correlated with the data from the pair of electrodes 750. When evaluating the data stored on the electrodes 750 and the monitoring device, the streams of data from the multiple sensor devices can be aligned according to the reference signals 835 also present in the streams of data. Once the streams of data are thus aligned, time offsets between the multiple sensor devices can be determined to allow the streams of data to be accurately correlated and compared.

The monitoring devices received by the five receptacles 740a-e may additionally include an accelerometer to collect data relating to motion events. In such cases, the use of the synchronization device 700 is not limited to sensing devices that collect data relating to electrocardio activity. Rather, the synchronization device 700 can synchronize sensing devices that implement different modalities to collect biometric data, e.g., an electrical modality for the ECG electrodes, a motion modality for the accelerometers, etc. As shown in FIGS. 7A-B, the synchronization device 700 transmits the reference signal 835 as an electrical signal to all sensing devices, e.g., the electrodes 750 and the monitoring devices. If the sensing devices implement different modalities, the example of synchronization device 700 demonstrates that, in some cases, a sensing device operating according to one modality (e.g., motion events) can be synchronized according to another modality (e.g., an electrical signal).

Although the synchronization device 700 transmits the reference signal 835 as an electrical signal, synchronization devices in general may employ any number and combination of modalities to synchronize sensing devices as described previously. For instance, if the monitoring devices can operate according to a motion modality, the receptacles 740*a-e* may generate a motion, instead of an electrical signal, to transmit a reference signal to the monitoring devices. For instance, the receptacles 740*a-e* may generate a rotation or shaking motion that the monitoring devices can detect and record as a distinctly identifiable event. The generation of this motion signal can occur with the generation of the electrical signal 835 to simultaneously synchronize the monitoring devices and the electrodes 750.

In the examples described above, the synchronization device 700 generates a reference signal 835 to provide a single synchronization data point for the sensing devices. It is understood, however, that additional synchronization data points may be employed to achieve better correlation of the data streams across multiple sensing devices. For instance, during or after the collection of electrocardio data with a pair of electrodes 750, a motion signal can be generated for detection by an accelerometer in the monitoring device to provide another synchronization data point. For instance, the patient may be instructed to jump up and down to move the monitoring device in a particular manner to generate the motion signal. Upon detecting the motion signal, the monitoring device may transmit a reference signal to the electrodes 750 to synchronize all sensing devices. Alternatively or additionally, the electrodes 750 may include their own accelerometers to detect the motion signal.

III. Wave Emission Timing

Synchronization waves in one modality may travel at a different velocity than synchronization waves in another modality. Light may travel at or near the speed of light, while pressure waves in the air (in the form of audio waves) may travel at approximately a millionth of that speed (at the speed of sound in air). Depending on the particular configuration and implementation, the timing with which synchronization pulses are emitted may depend on a known or estimated pulse transit time ("PTT" hereinafter)—that is, the time it takes a synchronization wave to travel from an emitter to a corresponding sensor.

In some embodiments, the slowest traveling waves may be emitted first to allow those waves the greatest length of time with which to travel toward corresponding sensors. After some delay, the next slowest waves may be emitted, and so on. With properly calculated timing based on accurate knowledge of the distance between emitters and sensors and the propagation velocities of waves in the various modalities, the emission of the waves may be staggered such that they all arrive at the sensors at or near a single point in time. Because the synchronization waves in the various modalities interact with respective sensors simultaneously, the time location of the synchronization wave interaction in the waveform data may serve as a basis for time-aligning waveform data recorded across multiple modalities.

Figure 2:
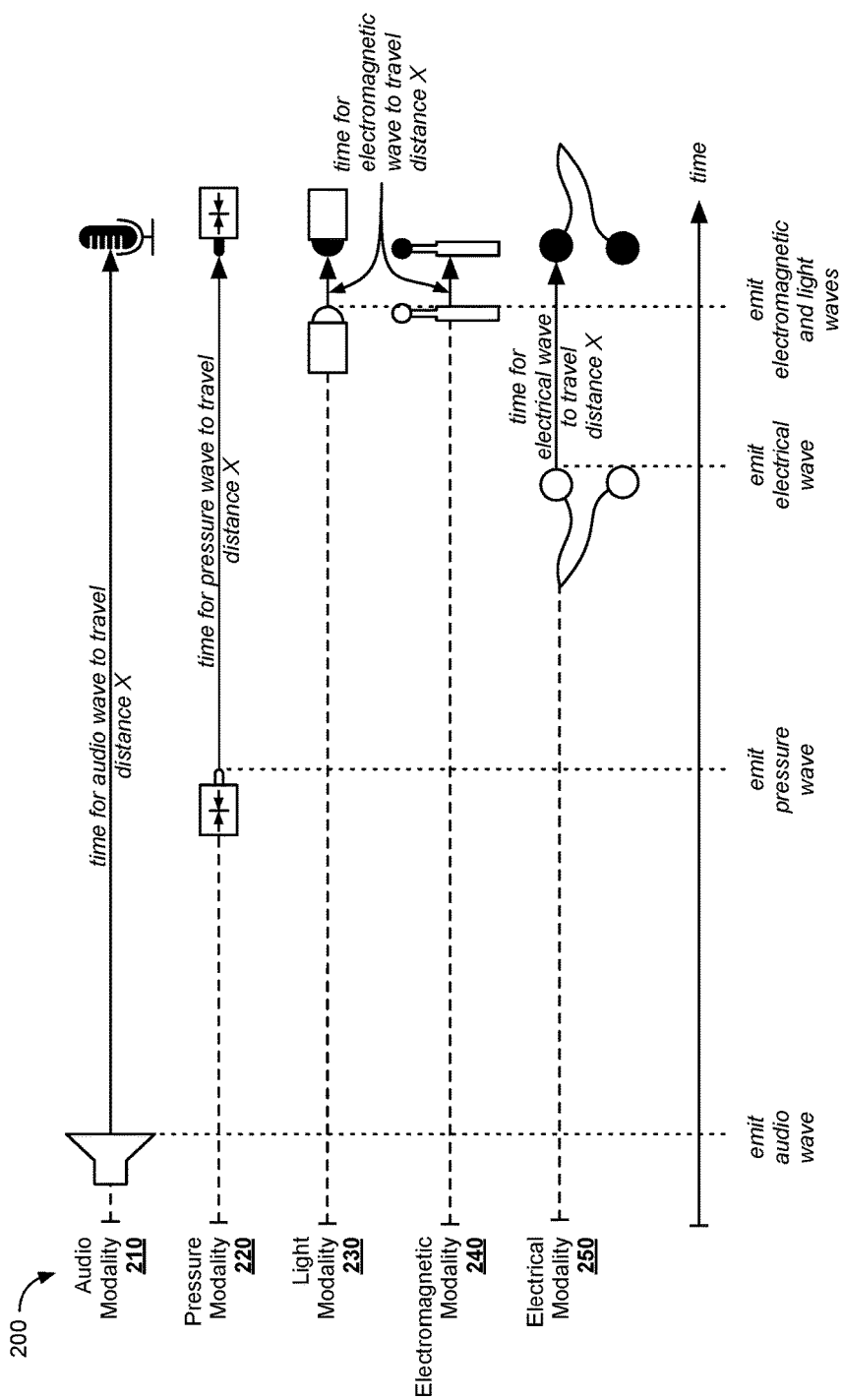
FIG. 2 is an example wave emission timing diagram, according to an example embodiment.

FIG. 2 is an example wave emission timing diagram 200. The horizontal line along the bottom of FIG. 2 illustrates a time axis, while each of the horizontal lines above the time axis illustrate the wave emission timing for a particular modality. Note that the time axis is not drawn to any particular scale, and is provided for explanatory purposes.

First, in the audio modality 210, an audio wave is emitted. In this example, the propagation velocity of an audio wave is slower than waves in other modalities. After some time, in the pressure modality 220, a pressure wave is emitted. In this example, the propagation velocity of a pressure wave in a liquid is faster than that of an audio wave, but is still slower than electrical and electromagnetic waves. After some additional time, in the electrical modality 250, an electrical wave is emitted. At this point in time, none of the already emitted waves (the audio wave, the pressure wave, and the electrical wave) still have not yet reached their respective sensors. At a later point in time, in the light modality 230 and the electromagnetic modality 240, a light wave and an electromagnetic wave are emitted. In this example, electromagnetic energy propagates at a greater velocity than the previously emitted waves.

Although the waves were emitted at different points in time, they all travel a distance of X by a particular point in time. To provide one illustrative example (which may not necessarily correlate to real-world velocities and timings), waves may travel in the audio modality 210 at 300 m/s, while waves in the light modality 230 travel at 300,000,000 m/s. If the distance between the audio emitter and microphone and the distance between the light emitter and light sensor are both 300 meters (for simplicity of calculation), then the audio wave would take 1 second to travel from the audio emitter and the microphone, while the light wave would take 1 microsecond (µs) to travel from the light emitter to the microphone. Thus, in this example, by emitting the audio wave, waiting 999,999 µs, then emitting the light wave, the waves will reach their respective sensors 1 second after emitting the audio wave. This example illustrates how accounting for PTT may improve the accuracy of waveform synchronization techniques described herein, particularly when wave propagation speed differs greatly between two or more modalities within a particular sensor network.

In some embodiments, static sensor configurations may permit the distances between synchronization emitters and sensors to be predetermined. In other embodiments, the distances between emitters and sensors may vary over time (e.g., statically-arranged emitters, and movable sensors, such as sensors coupled to a patient). Under such circumstances, the variance in emitter-sensor distances may be considered and noted, so that the data may be presented as accurate to within a threshold level of accuracy defined by that variance. In other circumstances, the distances between emitter-sensor pairs may be tracked, measured, and/or recorded over time; in this manner, measurements captured at or near a particular point in time may be correlated with a tracked emitter-sensor distance, thereby allowing the PTT to be determined. It should be understood that, in addition to wave emission timing techniques, other post-processing techniques may be performed to improve the accuracy of synchronization techniques described herein.

IV. Synchronization Waveform Segment Matching

In ad-hoc sensor networks, sensors may capture waveform data for short durations of time, followed by extended periods in which no data is recorded. Such practices are often utilized in order to reduce computational load and to improve battery life. Furthermore, some ad-hoc sensor networks may allow sensors to be added to the network while other sensors are already capturing and recording waveform data. While simple synchronization pulses or waves may be sufficient in some circumstances, a single pulse or repetitive wave may not provide enough context in order to synchronize measurements taken at sufficiently disparate points in time.

In some embodiments, a synchronization waveform may be a time-varying waveform that encodes information. In such embodiments, identifying a segment of the time-varying synchronization waveform from recorded waveform data may provide a contextual basis to enable time synchronization on a larger time scale.

Consider a known pseudo-random time-varying synchronization wave that is emitted for a period of 10 seconds. If a segment of that synchronization wave—where the beginning of the segment corresponds to a time of 5 seconds into the pseudorandom synchronization wave—is detected at the start of recorded waveform data of a particular sensor, then the waveform's time data may be modified or adjusted such that the time scale matches that of the synchronization wave. If the above-described process were repeated to generate time-synchronized waveform data of a different sensor, those two waveforms could be compared against a common time scale. Such alignment may be desired in order to understand the chain of events across multiple sensors, which would otherwise not be possible if the time data were not aligned. Furthermore, accurate alignment may allow certain events to be characterized based on the manner in which they propagate within various modalities.

Figure 3A:
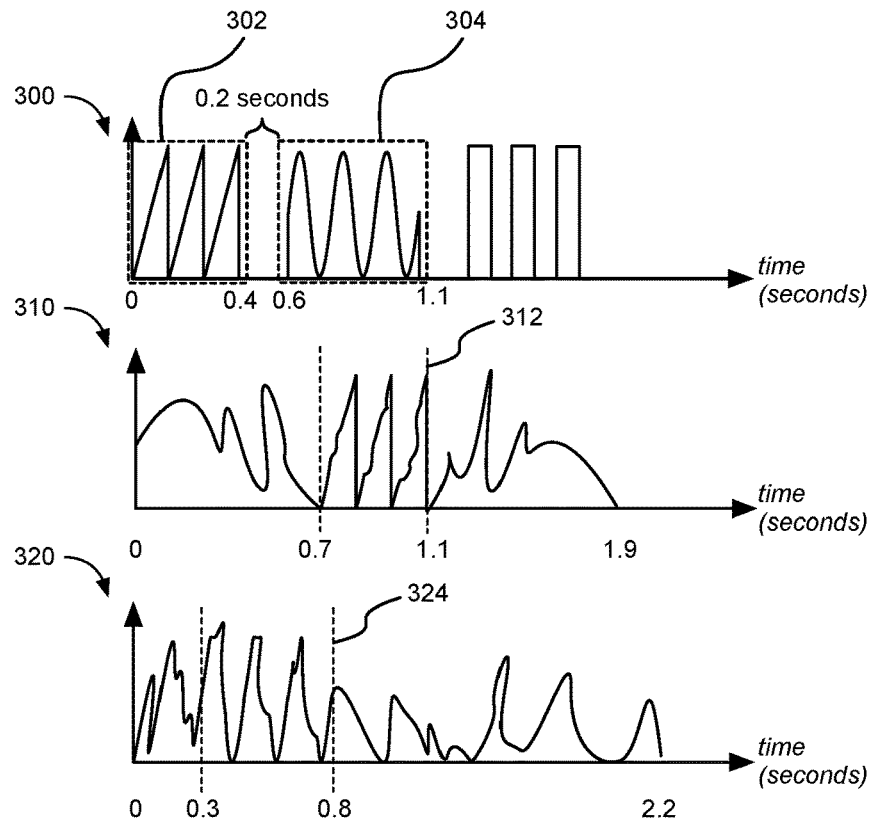
FIG. 3A illustrates an example time-varying synchronization waveform, according to an example embodiment.

FIG. 3A illustrates an example time-varying synchronization waveform 300, along with two captured waveforms 310, 320. In this example, the synchronization waveform 300 includes three distinct waveform segments: a sawtooth segment 302 (from 0 to 0.4 seconds), a sinusoidal segment 304 (from 0.6 to 1.1 seconds), and a square segment. Here, the end of the sawtooth segment 302 and the start of the sinusoidal segment 304 are separated by 0.2 seconds. In this example, the synchronization waveform 300 was emitted, a portion of which was captured by one sensor to produce the waveform 310, and another portion of which was captured by another sensor to produce the waveform 320.

More specifically, a portion 312 of the waveform 310 is indicative of the segment 302. Although noise and other measurements may be recorded in conjunction with the sawtooth segment 302, the sawtooth segment 302 may be identified using filters or other computational techniques (e.g., digital signal processing techniques). The portion 312 is present within waveform 310 from 0.7 to 1.1 seconds, with respect to the start of waveform 310.

Additionally, a portion 324 of the waveform 320 is indicative of the segment 324. Although noise and other measurements may be recorded in conjunction with the sinusoidal segment 304, the sinusoidal segment 304 may be identified using filters or other computational techniques (e.g., digital signal processing techniques). The portion 324 is present within waveform 320 from 0.3 to 0.8 seconds, with respect to the start of waveform 320.

Figure 3B:
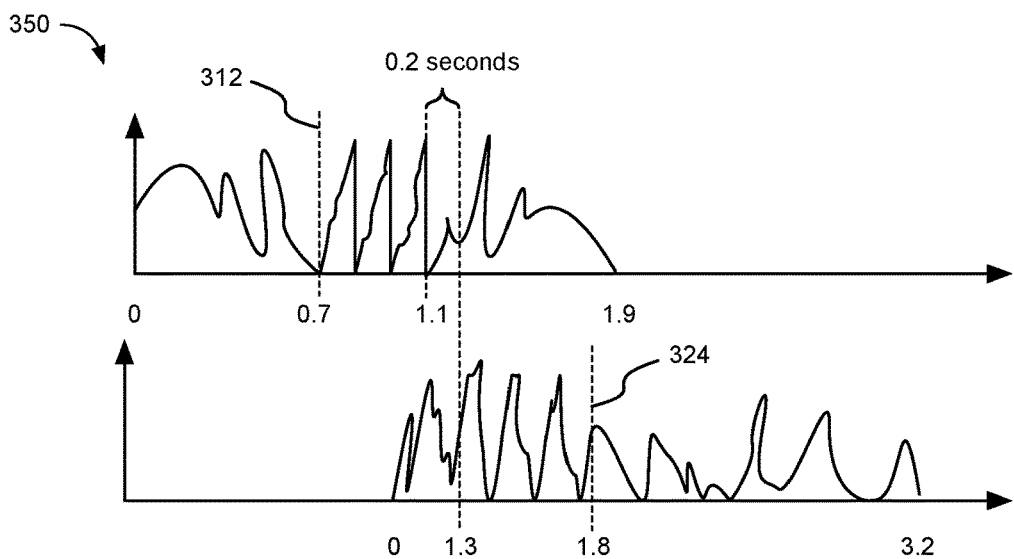
FIG. 3B illustrates an example synchronization technique using segment matching, according to an example embodiment.

FIG. 3B illustrates an example synchronization technique using segment matching. In the stacked set of graphs 350, the waveform 310 and waveform 320 are aligned in time based on the identified segments as described above. Because the synchronization waveform 300 and the timing of its segments are known, it can be determined that the start of portion 324 in waveform 320 begins 0.2 seconds after the end of the portion 312 in waveform 310. As a result, a computational process may shift the time values of waveform 320 so that the portion 312 and the portion 324 are aligned according to the timing of synchronization waveform 300. Here, because the portion 312 ends at 1.1 seconds in waveform 310, and because the segment 304 is known to begin 0.2 seconds after the end of segment 302, the start of portion 324 is determined to begin at 1.3 seconds (relative to the start of waveform 310). The time alignment of waveform 310 and 320 is illustrated in FIG. 3B. After time alignment, the relative timing of events across waveform 310 and waveform 320 can be evaluated.

In some implementations, waveform synchronization may involve modifying the time values mapped to waveform data. Time value modification may involve shifting the time values, overwriting the time values, and adding a second set of time values to the waveform data (so that the original time data values are preserved), among other possible techniques. In other implementations, waveform synchronization may involve producing a graphical representation of two or more waveforms that are aligned in time to enable a user to visually compare those waveforms. In some cases—such as those where clock drift causes recorded time intervals between waveform data points to be smaller than or greater than the actual time intervals between those points—graphically modifying the waveform data may involve "compressing" or "stretching" the waveforms (i.e., scaling the time values to produce a graph of the waveform that appears compressed or stretched compared to the non-scaled waveform). A graphical output may take the form of a physical print out, as well as a graphical depiction on a display device such as a television or computer monitor.

In further implementations, synchronizing waveform data may be an intermediate step of a more comprehensive analysis. For example, a computational process may employ the waveform synchronization techniques described herein before performing further analyses, such as characterizing certain phenomena, determining time intervals between events and/or across multiple modalities, and determining a causal chain of events across multiple sensors. Thus, the resulting output of waveform synchronization as described herein may be modified waveform data, data that characterizes the manner in which to compare the waveform data, or a graphical output of time-aligned waveforms.

Identifying a segment of a waveform—including determining the boundaries of the segment (i.e., starting and ending positions, as indicated by vertical dashed lines in FIGS. 3A and 3B)—may be achieved using a variety of computing techniques. As one example, if a synchronization waveform is a single frequency, Fast Fourier transforms (FFTs) or discrete Fourier transforms (DFTs) may be utilized in order to identify a point in time when the frequency of the synchronization waveform appears in recorded waveform data. Other frequency analyses using FFTs and/or DFTs may also be performed to identify more complex synchronization waves.

Additionally, some computational processes may be employed on either the waveform data or some transformation thereof in order to identify the synchronization waveform pattern (or a segment of the synchronization waveform). Referring back to FIG. 3A, a low-pass filter may first be applied to waveform 310 to smooth out the small ripples in the portion 312. Then, that portion may be analyzed and compared to known features of sawtooth segment 302. For instance, the sawtooth segment 302 rises over a period of time (approximately 0.133 seconds), then rapidly drops, and repeats three times. A digital analysis of portion 312 may determine such rise times, drop times, and number of repeats; if those values match or are close (i.e., within a threshold tolerance) to the known features of the sawtooth segment 302, then the computational process could determine that the portion 312 matches the sawtooth segment 302.

It should be understood that the segment matching-based waveform synchronization example depicted in FIG. 3A and FIG. 3B is one example provided for explanatory purposes. In some instances, a segment of a synchronization wave may or may not be as visually apparent as shown in FIG. 3A and FIG. 3B. Identifying such segments may involve filtering and DSP techniques in order to isolate the segment or to more accurately analyze the waveform.

V. Example Methods

Figure 4:
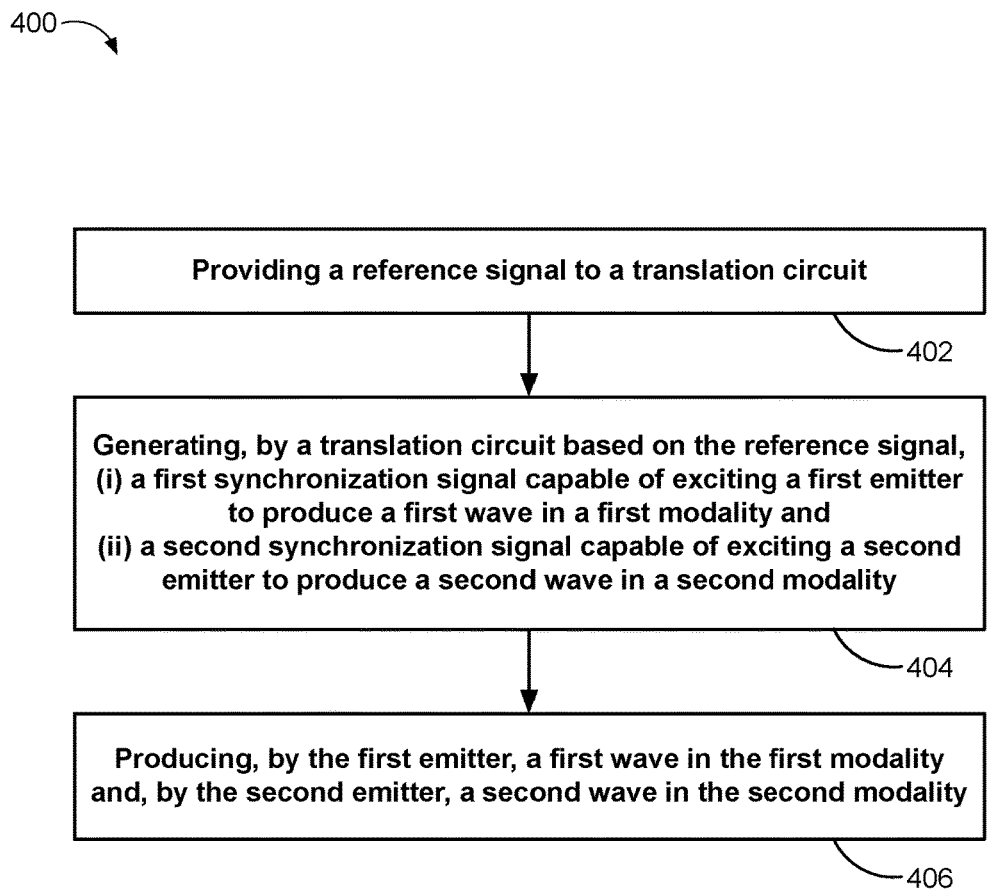
FIG. 4 is a flowchart of an example method of, according to an example embodiment.

FIG. 4 is a flowchart of operations 400 for facilitating multi-modality sensor synchronization, according to an example implementation. Operations 400 shown in FIG. 4 present an implementation that could be utilized within system 100 of FIG. 1, for example, or more generally by other sensor networks, computing devices, or control systems. Operations 400 may include one or more actions as illustrated by blocks 402-406. Although the blocks are illustrated in sequential order, these blocks may also be performed in parallel, and/or in a different order than those described herein. Also, the various blocks may be combined into fewer blocks, divided into additional blocks, and/or removed based upon the directed implementation.

In addition, the operations 400 and other operations disclosed herein show functionality of one possible implementation. In this regard, each block may represent a module, a segment, or a portion of program code, which includes one or more instructions executable by a processor or computing device for implementing specific logical operations or steps. The program code may be stored on any type of computer-readable medium, for example, such as a storage device included in a disk or hard drive. The computer-readable medium may include a non-transitory computer-readable medium, for example, such as computer-readable media that stores data for short periods of time like register memory, processor cache and/or random access memory (RAM). The computer-readable medium may also include non-transitory media, such as secondary or persistent long-term storage, like read-only memory (ROM), optical or magnetic disks, and compact-disc read-only memory (CD-ROM), for example. The computer-readable media may be considered a computer-readable storage medium, for example, or a tangible storage device.

In addition, one or more blocks in FIG. 4 may represent circuitry that is wired to perform the specific logical operations.

A. Provide a Reference Signal

Block 402 involves providing a reference signal to a translation circuit. As described above, the reference signal may be an analog signal or a digital signal. The amplitude and/or frequency of the reference signal may vary over time, the variance of which may be random, pseudorandom, or an encoding of a sequence of bits.

"Providing" the reference signal may involve generating the reference signal, then sending that generated reference signal over to the translation circuit. Generating the reference signal may including driving an oscillator to produce a frequency (or carrier frequency), encoding digital information into an analog signal (e.g., using AM, FM, or other data modulation techniques), sampling certain devices that measure environmental conditions to obtain pseudorandom information (i.e., thermal noise), and/or any combination thereof. In various embodiments, the provided reference signal or the information encoded therein may be stored and used in post-processing waveform synchronization processes.

B. Generate Multi-Modality Synchronization Signals

Block 404 involves generating, by a translation circuit based on the reference signal, a first synchronization signal capable of exciting a first emitter to produce a first wave in a first modality and a second synchronization signal capable of exciting a second emitter to produce a second wave in a second modality. As described herein, a signal defined to be "capable of exciting" an emitter to produce a wave in a particular modality may be a signal possessing characteristics that interact with or cause the excitation of such an emitter. In some instances, an emitter may be designed to operate within a range of amplitudes and frequencies, and a signal "capable of" exciting such an emitter may be a signal whose amplitudes and frequencies comply with (or at least substantially comply with) those operational ranges.

Here, the translation circuit may generate the synchronization signals by converting the reference signal into corresponding synchronization signals that both reflects the characteristics of the reference signal and adheres to the operational capabilities of the respective emitters and sensors. In other words, if the reference signal possesses certain time-varying qualities (e.g., data encoded via AM or FM), the generated synchronization signal may preserve those time-varying qualities (which may be scaled or adjusted so as to at least substantially adhere to a particular modality).

As one example, a reference signal might include AM information with peak-to-peak variance of −1 V to 1 V. An example modality—such as a light modality utilizing an incandescent light bulb—might define an operational voltage range of 0 V to 120 V. In this example, the reference signal might be shifted up to vary from 0 V to 2 V, then be scaled by a factor of 60 in order to conform to that particular modality. Another example modality—such as a light modality utilizing an LED—might define an operational voltage of 0 V and 3 V, where any voltage below 3 V would result in the LED being turned off. Here, the conversion might involve digitally sampling the AM reference signal, then simulating the AM signal using PWM to effectively vary the brightness of the LED.

It should be understood that the operations 400 may involve generating any number of synchronization signals to be provided to any number of corresponding emitters. In some cases, multiple synchronization signals may be provided to a single emitter; in other cases, a single synchronization signal may be provided to multiple emitters.

C. Produce Multi-Modality Waves

Block 406 involves producing, by the first emitter, a first wave in the first modality and, by the second emitter, a second wave in the second modality. Producing a modality-specific wave with a corresponding emitter may involve exciting the emitter with the received modality-specific signal from the translation circuit. An emitter may include a transducer that facilitates the conversion from the modality-specific signal (e.g., an electrical signal) to waves in a particular modality.

As a specific example, an emitter might include a magnetic element and a membrane which collectively form a speaker. An audio signal from the translation circuit may energize the magnetic element, which in turn causes the membrane to vibrate the membrane. The vibration of the membrane may in turn generate waves in the air to produce the audio waves. Thus, "producing" a modality-specific wave may involve multiple transformations (e.g., electrical to magnetic, then magnetic to mechanical, as described in the above example).

In addition to blocks 402, 404, and 406, other operations may be performed, depending upon the particular implementation. In some embodiments, additional steps may be employed to generate and store the reference signal.

Additionally, the translation circuit may be configured (or its operational parameters may be otherwise altered) before performing the conversion. Depending on the circumstances, the translation circuit may vary the manner of conversion so that the signals provide an adequate amount of emitter excitation to produce waves of sufficient amplitude that can be detected by sensors. In some embodiments, the translation circuit may include sub-circuits for particular modalities that may be selectively activated and deactivated, depending on the configuration of a sensor network. As one example scenario, a new sensor may be added to an ad-hoc sensor network while the rest of the sensors in the network are operating. Upon the addition of the new sensor, its modality information may be conveyed to the translation circuit (either directly, over a network, via a cloud service, etc.). Upon receiving an indication that the new sensor has been added to the network, the translation circuit may responsively activate (and possibly configure) a sub-circuit to begin generating synchronization signals to excite an emitter for producing synchronization waves within the modality of the new sensor.

Some other additional operations include instructing the translation circuit (or at least of sub-circuit within the translation circuit) to modify the manner of conversion between the reference signal and a corresponding modality-specific signal. Information about the signal generator, its parameters, the reference signal it produces, the manner of operation of the translation circuit, timing delays of the translation circuit, and/or any other operational parameter may be provided to and stored by separate computing devices (either integrated within the system, present within a network, or accessible via a cloud service). The operational data may serve as a basis for post-processing wave synchronization.

VI. Multi-Modality Sensing Device Synchronization

Some sensing devices may include multiple sensors for measuring disturbances in multiple modalities. In some configurations, a sensor network may contain multi-modal sensing devices that share a common sensing modality. For example, a set of sensing devices may, in addition to detecting disturbances in a modality, may all be equipped with accelerometers or other motion sensors. Each of these sensing devices may operate according to its own independent clock, which drives both the modality-specific sensor and the accelerometer. In such scenarios, events that occur in one modality (e.g., motion events detected by the accelerometers) may serve as a basis for time-aligning waveforms recorded by different sensing devices.

Figure 5:
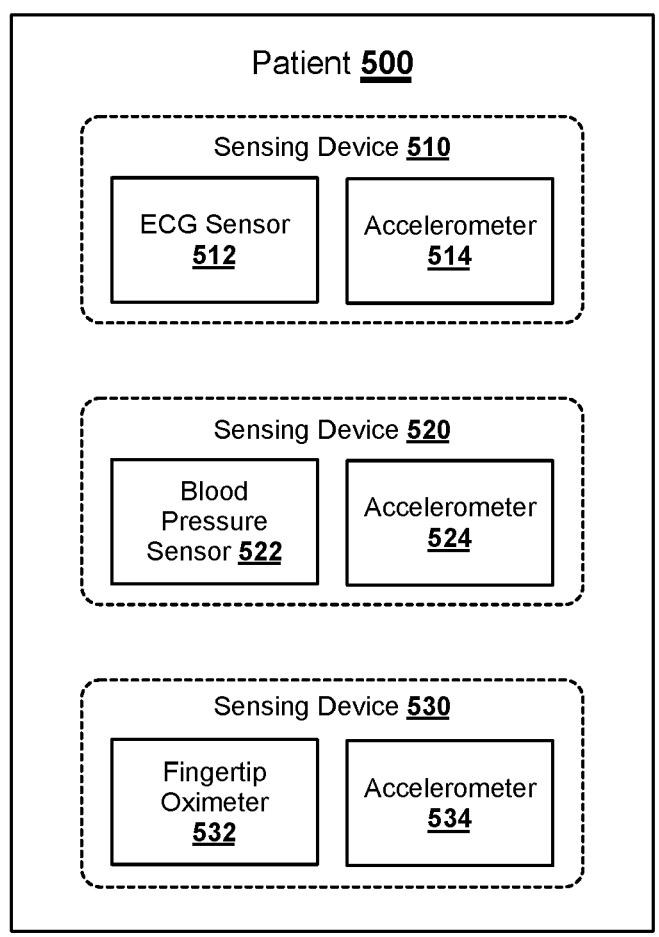
FIG. 5 is a schematic block diagram of an example system, according to an example embodiment.

FIG. 5 illustrates a schematic block diagram of an example sensing device configuration. In this example, patient 500 may be coupled to sensing devices 510, 520, and 530. Sensing device 510 includes ECG sensor 512 and accelerometer 514. Sensing device 520 includes blood pressure sensor 522 and accelerometer 524. Sensing device 530 includes fingertip oximeter 532 and accelerometer 534.

During operation, the sensing devices 510, 520, and 530 may record ECG data, blood pressure data, and oxygen saturation data of the patient 500, respectively. One technique for time-aligning data captured by sensing devices 510, 520, and 530 may involve simultaneously recording acceleration data, which may be mapped directly to waveform data captured by the respective sensing device. For example, each ECG sensor waveform data point may be mapped to a relative time value (as determined from the clock of sensing device 510) and may also be mapped to an acceleration value. Certain acceleration events (e.g., peaks in the acceleration, known acceleration patterns, etc.) may provide a basis for aligning sensor waveform data across multiple modalities.

As a specific example, patient 500 may be instructed to jump up and down a certain number of times. The movement of patient 500 may be captured by accelerometers 514, 524, and 534. An event (e.g., the patient 500 reaching peak height during the jump or the patient 500 landing on the ground) may produce peaks in acceleration data that are common to the sensing devices 510, 520, and 530. In effect, such intentionally-produced acceleration on a sensing device may be similar the synchronization waveforms as described in the present application (or, at least serves a similar function in waveform time-alignment synchronization).

Various circumstances and patient movements (either intentional or involuntary) may produce the acceleration events described above. For example, a patient's cardiovascular health may be evaluated using multiple sensors, each of which could be equipped with accelerometers. If the patient walks or runs on a treadmill, regularly occurring acceleration events (e.g., footsteps) might serve as a basis for waveform alignment.

Modalities other than acceleration sensing may serve as the basis for waveform alignment. For instance, each sensing device may be equipped with a microphone, and auditory events may be produced (either with a speaker, from a patient action such as clapping or through a patient's voice). It should be understood that any modality commonly sensed among multiple sensing devices may serve as the modality through which common events may be used for waveform alignment.

Furthermore, two or more of the above-described techniques may be combined in order to improve the accuracy of waveform alignment. For example, an electrical synchronization wave, along with an acceleration event, may be provided to the sensing device 510. Post-processing synchronization processes may then utilize the electrical synchronization wave captured by the ECG sensor 512, the acceleration event detected by the accelerometer 514, and/or a combination of the two in order to time-align the ECG data to waveform data captured by other sensors.

VIII. Example Computer-Readable Medium

Figure 6:
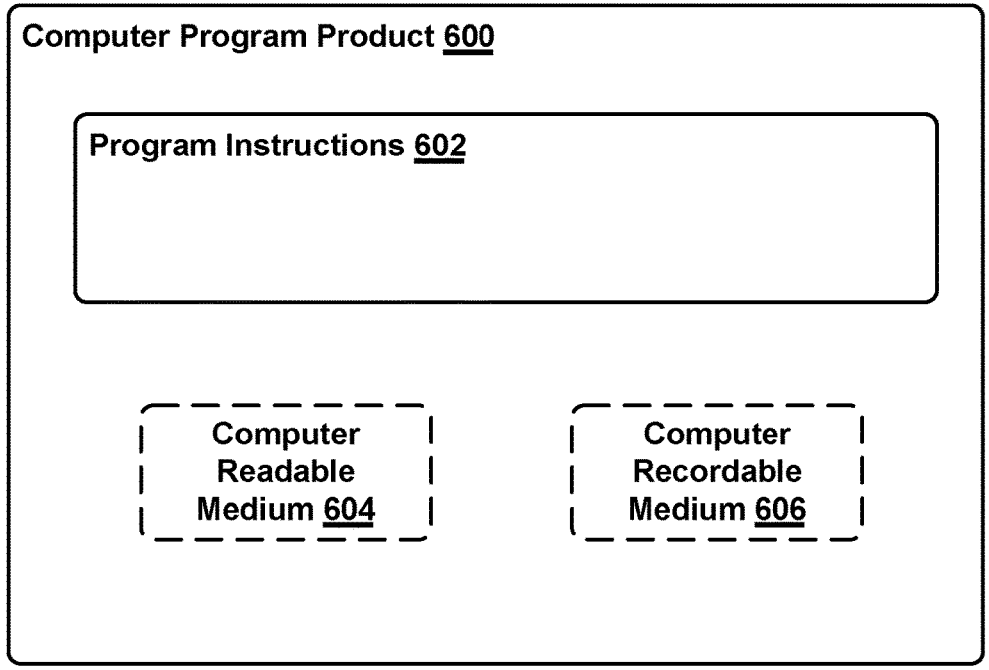
FIG. 6 is an example computer-readable medium, according to an example embodiment.

In some embodiments, the disclosed methods may be implemented as computer program instructions encoded on a computer-readable storage media in a machine-readable format, or on other non-transitory media or articles of manufacture. FIG. 6 illustrates an example computer readable medium in the form of a computer program product 600 that includes a computer program for executing a computer process on a computing device. In one embodiment, the example computer program product 600 is provided using a signal bearing medium 601. The signal bearing medium 601 may include one or more program instructions 602 that, when executed by one or more processors may provide functionality or portions of the functionality described above with respect to FIGS. 1-5. Thus, for example, referring to the embodiments shown in FIG. 4, one or more features of blocks 402-406 may be undertaken by one or more instructions associated with the signal bearing medium 601.

In some examples, the signal bearing medium 601 may encompass a computer-readable medium 603, such as, but not limited to, a hard disk drive, a Compact Disc (CD), a Digital Video Disk (DVD), a digital tape, memory, etc. In some implementations, the signal bearing medium 601 may encompass a computer recordable medium 604, such as, but not limited to, memory, read/write (R/W) CDs, R/W DVDs, etc. In some implementations, the signal bearing medium 601 may encompass a communications medium 605, such as, but not limited to, a digital and/or an analog communication medium (e.g., a fiber optic cable, a waveguide, a wired communications link, a wireless communication link, etc.). Thus, for example, the signal bearing medium 601 may be conveyed by a wireless form of the communications medium 605 (e.g., a wireless communications medium conforming to the IEEE 802.11 standard or other transmission protocol).

The one or more programming instructions 602 may be, for example, computer executable and/or logic implemented instructions. In some examples, a computing device such as the computing device described with respect to FIGS. 1-5 may be configured to provide various operations, functions, or actions in response to the programming instructions 602 conveyed to the computing device by one or more of the computer readable medium 603, the computer recordable medium 604, and/or the communications medium 605. It should be understood that arrangements described herein are for purposes of example only. As such, those skilled in the art will appreciate that other arrangements and other elements (e.g., machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

The above detailed description describes various features and functions of the disclosed systems, devices, and methods with reference to the accompanying figures. While various aspects and embodiments have been disclosed herein, other aspects and embodiments will be apparent. The various aspects and embodiments disclosed herein are for purposes of illustration and are not intended to be limiting, with the true scope being indicated by the following claims.

What is claimed is:

1. A method comprising:
providing a reference signal to a translation circuit;
generating, by the translation circuit based on the reference signal, (i) a first synchronization signal capable of exciting a first emitter to produce a first wave in a first modality and (ii) a second synchronization signal capable of exciting a second emitter to produce a second wave in a second modality, wherein a modality is a domain within a form of energy, and wherein the first modality is different from the second modality; and
producing, by the first emitter, the first wave in the first modality and, by the second emitter, the second wave in the second modality, wherein the first wave is substantially directed toward a first physiological sensor configured to receive the first wave and to associate a first sensed physiological parameter with a received portion of the first wave, and wherein the second wave is substantially directed toward a second physiological sensor configured to receive the second wave and to associate a second sensed physiological parameter with a received portion of the second wave.

2. The method of claim 1, wherein providing the reference signal comprises:
generating, by a signal generator, the reference signal, wherein the reference signal is capable of being transmitted within a third modality; and
transmitting the reference signal to the translation circuit over the third modality.

3. The method of claim 2, wherein generating the reference signal comprises:
generating the reference signal based on a time encoding of a pseudorandom sequence.

4. The method of claim 2, wherein generating the reference signal comprises:
generating the reference signal based on a time encoding of a known sequence of values.

5. The method of claim 1, wherein the reference signal has a reference frequency, and wherein generating the first synchronization signal comprises:
converting the reference signal from the reference frequency to a first frequency to generate the first synchronization signal, wherein the first frequency is within the domain defined by the first modality.

6. The method of claim 1, wherein the reference signal has a reference amplitude, and wherein generating the first synchronization signal comprises:
amplifying the reference signal from the reference amplitude to a first amplitude to generate the first synchronization signal, wherein the first amplitude is within a threshold range of amplitudes within the domain defined by the first modality.

7. The method of claim 1, wherein the reference signal is an analog signal, and wherein generating the first synchronization signal comprises:
sampling the reference signal to generate reference data representative of the reference signal; and
generating, as the first synchronization signal, a digital signal as a pulsed modulation of the reference data.

8. The method of claim 1, wherein the reference signal is a digital signal including digital data, and wherein generating the first synchronization signal comprises:
generating, as the first synchronization signal, an analog signal based on the digital data within the digital signal.

9. The method of claim 1, wherein producing the first wave and the second wave comprises:
causing the first emitter to produce the first wave at a first time; and
causing the second emitter to produce the second wave at a second time, wherein the second time occurs after the first time.

10. The method of claim 9, further comprising:
determining the second time based at least in part on known propagation velocities of the first wave and the second wave.

11. A system comprising:
a signal generator operable to generate a reference signal;
a translation circuit operable to convert the reference signal into a first synchronization signal and a second synchronization signal, wherein the first synchronization signal includes characteristics that excite emitters in a first modality, wherein the second synchronization signal includes characteristics that excite emitters in a second modality, wherein a modality is a domain within a form of energy, and wherein the first modality is different from the second modality;

a first emitter operable to receive the first synchronization signal and responsively produce a first synchronization wave in a first modality, wherein the first synchronization wave is to be directed toward a first physiological sensor configured to receive the first synchronization wave and to associate a first sensed physiological parameter with a received portion of the first synchronization wave; and a second emitter operable to receive the second synchronization signal and responsively produce a second synchronization wave in a second modality, wherein the second synchronization wave is to be directed toward a second physiological sensor configured to receive the second synchronization wave and to associate a second sensed physiological parameter with a received portion of the second synchronization wave.

12. The system of claim 11, wherein the signal generator and the translation circuit are electrically coupled by a transmission medium, and wherein the reference signal is provided to the translation circuit via the transmission medium.

13. The system of claim 11, wherein the translation circuit and the first emitter are electrically coupled by a transmission medium, and wherein the first synchronization signal is provided to the first emitter via the transmission medium.

14. The system of claim 11, wherein the first physiological sensor includes a first clock, wherein the second physiological sensor includes a second clock, and wherein the first clock is different from the second clock.

15. The system of claim 11, further comprising:
a storage medium operable to store information output from a first sensor and a second sensor.

16. The system of claim 11, further comprising the first or second physiological sensor.

17. A method comprising:
producing, by a first emitter, a first wave in a first modality;
producing, by a second emitter, a second wave in a second modality, wherein a modality is a domain within a form of energy, and wherein the first modality is different from the second modality;
capturing, by a first physiological sensor, a first segment of a first waveform including at least a portion of the first wave and first sensed physiological information, wherein the first segment begins at a first time offset relative to the start of the first waveform;
capturing, by a second physiological sensor, a second segment of a second waveform including at least a portion of the second wave and second sensed physiological information, wherein the second segment begins at a second time offset relative to the start of the second waveform; and
based on at least the first time offset and the second time offset, providing a time-synchronized output indicative of at least one of (i) a portion of the first waveform and the first sensed physiological information and (ii) a portion of the second waveform and the first sensed physiological information.

18. The method of claim 17, further comprising:
generating, by a translation circuit based on a reference signal, (i) a first synchronization signal that interacts with the first emitter to produce the first wave in the first modality and (ii) a second synchronization signal that interacts with the second emitter to produce the second wave in the second modality.

19. The method of claim 18, further comprising:
generating, by a signal generator, the reference signal; and
providing the reference signal to the translation circuit.

20. The method of claim 17, wherein providing the time-synchronized output comprises:
producing, by an image forming apparatus, a graphical depiction of the portion of the first waveform and the portion of the second waveform on a printing medium.

21. The method of claim 17, wherein providing the time-synchronized output comprises:
producing, by an image forming apparatus, a graphical representation of the portion of the first waveform and the portion of the second waveform on a display device.

22. A system comprising:
a signal generator operable to generate a reference signal; and
a synchronization device coupled to the signal generator and configured to receive the reference signal from the signal generator, the synchronization device including a plurality of receptacles, each receptacle of the plurality of receptacles configured to physically engage with a physiological sensing device and transmit the reference signal simultaneously with the other receptacles, one or more of the physiological sensing devices, when engaged, being configured to detect and store the reference signal with a respective timestamp, wherein each respective timestamp indicates a time offset for data collected by the respective physiological sensing device.

23. The system of claim 22, wherein the synchronization device transmits the reference signal to the plurality of receptacles as an electrical waveform.

24. The system of claim 23, wherein the synchronization device includes a base and a top plate, the base including the plurality of receptacles, the top plate configured to be assembled over the base when one or more physiological sensing devices are disposed in respective receptacles between the base and the top plate.

25. The system of claim 23, wherein at least one of the physiological sensing devices includes electrocardiogram (ECG) electrodes.

26. The system of claim 22, wherein the physiological sensing devices includes at least one first physiological sensing device operable to detect signals according to a first modality and at least one second physiological sensing device operable to detect signals according to a second modality.

27. The system of claim 26, wherein the synchronization device transmits the reference signal to the at least one first physiological sensing device according to the first modality and the at least one second physiological sensing device according to the second modality.

28. The system of claim 26, wherein the at least one second physiological sensing device is further operable to detect signals according to the first modality, and the synchronization device transmits the reference signal to the at least one first physiological sensing device and the at least one second physiological sensing device according to the first modality.

* * * * *